United States Patent
Jönsson

(10) Patent No.: US 9,826,964 B2
(45) Date of Patent: Nov. 28, 2017

(54) DEVICE, KIT AND METHOD FOR CLOSURE OF A BODY LUMEN PUNCTURE

(75) Inventor: Anders Jönsson, Bromma (SE)

(73) Assignee: ITSO Medical AB, Helsingborg (SE)

( * ) Notice: Subject to any disclaimer, the term of this patent is extended or adjusted under 35 U.S.C. 154(b) by 295 days.

(21) Appl. No.: 13/414,691

(22) Filed: Mar. 7, 2012

(65) Prior Publication Data

US 2012/0302987 A1   Nov. 29, 2012

Related U.S. Application Data

(63) Continuation of application No. PCT/EP2010/063135, filed on Sep. 7, 2010.

(60) Provisional application No. 61/240,273, filed on Sep. 7, 2009.

(30) Foreign Application Priority Data

Sep. 7, 2009   (EP) .................................. EP09169672

(51) Int. Cl.
   *A61B 17/03*   (2006.01)
   *A61M 5/00*   (2006.01)
   *A61B 17/00*   (2006.01)

(52) U.S. Cl.
   CPC   *A61B 17/0057* (2013.01); *A61B 2017/00579* (2013.01); *A61B 2017/00597* (2013.01); *A61B 2017/00637* (2013.01); *A61B 2017/00659* (2013.01); *A61B 2017/00889* (2013.01); *A61B 2017/00893* (2013.01)

(58) Field of Classification Search
   CPC ...... A61B 17/0057; A61B 2017/00659; A61B 2017/00637; A61B 2017/00597

USPC .......................... 606/159, 213; 604/48, 57; 623/1.13–1.15, 1.18
See application file for complete search history.

(56) References Cited

U.S. PATENT DOCUMENTS

| | | | |
|---|---|---|---|
| 6,833,003 B2 | 12/2004 | Jones et al. | |
| 2003/0181942 A1* | 9/2003 | Sutton | 606/200 |
| 2008/0319475 A1* | 12/2008 | Clark | 606/213 |
| 2009/0143815 A1 | 6/2009 | Eidenschink et al. | |

FOREIGN PATENT DOCUMENTS

| | | |
|---|---|---|
| DE | 10 2006 050385 A1 | 4/2008 |
| EP | 1 046 375 A1 | 10/2000 |
| WO | WO 00/18301 A1 | 4/2000 |

(Continued)

*Primary Examiner* — Anh Dang
(74) *Attorney, Agent, or Firm* — Inskeep IP Group, Inc.

(57) ABSTRACT

A medical device and method for closure of a puncture in a body lumen are disclosed. The device has an aggregate (10) of a support structure (20) and a substantially fluid tight patch member (30) attached thereto at an attachment unit (40). The aggregate has a first, temporary delivery shape, for delivery to an interior of said body lumen and to be subsequently subjected to a change of shape to a second shape, which is a tubular shape. When delivered in said body lumen, the patch member is arranged radially outside of said tubular support structure and arranged towards an inner tissue wall of the body lumen. The aggregate is the detached from a delivery device and said puncture is intraluminally closed in a leakage tight manner, advantageously supported by a physiological pressure of a body fluid in said body lumen. The device may biodegrade over time.

22 Claims, 17 Drawing Sheets

(56) References Cited

FOREIGN PATENT DOCUMENTS

| WO | WO 2005/034764 A1 | 4/2005 | |
|----|-------------------|--------|---|
| WO | WO 2006/034114 A2 | 3/2006 | |
| WO | WO 2006/125022 A2 | 11/2006 | |
| WO | WO 2007131553 A1 * | 11/2007 | ............ A61B 17/22 |
| WO | WO 2008/022327 A2 | 2/2008 | |
| WO | WO 2008/024491 A1 | 2/2008 | |
| WO | WO 2008/112500 A2 | 9/2008 | |
| WO | WO 2009/007939 A2 | 1/2009 | |

\* cited by examiner

DEVICE, KIT AND METHOD FOR CLOSURE OF A BODY LUMEN PUNCTURE

RELATED APPLICATIONS

This application is a continuation of and claims priority to International Patent Application No. PCT/EP2010/063135, International Filing Date 7 Sep. 2010, entitled Device, Kit And Method For Closure Of A Body Lumen Puncture, which claims priority to European Patent Application No. EP09169672.4 filed 7 Sep. 2009 entitled Device, Kit And Method For Closure Of A Body Lumen Puncture, and to U.S. Provisional Application Ser. No. 61/240,273 filed 7 Sep. 2009 entitled Device, Kit And Method For Closure Of A Body Lumen Puncture, all of which are hereby incorporated herein by reference in their entireties.

FIELD OF THE INVENTION

This invention pertains in general to the field of medical devices and methods for closure of punctures in body lumina, such as a vessel, in a patient. More particularly, the invention relates to the field of sealing apertures created by medical procedures that pierce the walls of blood vessels in living tissue.

BACKGROUND OF THE INVENTION

During certain types of medical surgery or treatment, an introducer is used to access the vascular system of a patient. The introducer is inserted through the wall of a blood vessel in order to obtain access to the vascular system and may thereafter be used for guiding medical instruments such as catheters, guide wires and the like.

After completion of the medical procedure, there will be an incision or a wound in the wall of the blood vessel corresponding to the size of the introducer. The bleeding from the wound, which is a result of such a surgical operation, can be stopped by applying direct pressure on the wound. However, applying direct pressure on the wound will require assistance of medical personnel and may also restrict the flow of blood through the vessel. Ischemia may occur and can lead to serious consequences.

In cases of puncturing the femoral arteries, the required time may be as long as about 45 minutes or more and in some cases re-bleeding occurs if the patient is not in rest. Bleeding from a vessel puncture in a substantially sized blood vessel can be severe.

A variety of methods and devices have been suggested for replacing the traditional method disclosed above, some of which involve introducing chemical compounds which act as homeostasis catalysts or as adhering agents, whilst others aim at introducing various forms of plugging members into the puncture.

Sealing devices in form of sealing plugs in the cutaneous channel at the puncture site outside the vessel are known, e.g. from US patent application 2009/0054926 or European patent EP 1349501. However, the blood pressure inside the vessel may press the plug out of position before a reliable sealing has occurred.

Other sealing devices in form of double button type fasteners that are affixed to each other, in the type of an outside member and inside member in relation to the lumen and a crosspiece arranged across the puncture opening, both inside and outside of the vessel wall are known, e.g. from U.S. Pat. No. 7,488,340, or U.S. Pat. No. 7,572,274. The outside member and inside member are brought in a locked configuration upon assembly and compress the vessel wall tissue around the puncture opening.

However, such button type sealing devices may not seal off the puncture optimally.

For instance, such button type devices may restrict the lumen and blood flow therein. The inside member of the device protruding into the blood vessel often substantially restricts the patency of the lumen. This is in particular the case for small diameter lumen, such as at peripheral vessels. A protruding member may also lead to a turbulent flow, which might cause secondary effects, such as creation of thrombosis or embolies.

Furthermore, the devices may damage the vessel wall, in particular in the case of peripheral vessels, such as the arteria subclavia, the arteria axillaris, which for instance are accessed in the region of the clavicle, or the arteria radialis for access in the arm, which all are brittle vessels.

The aforementioned double sided tissue compression of the vessel wall causes a pressure onto the wall tissue, which brings about a number of issues.

For instance, the vessel wall may be damaged when the applied compression or pressure is too high. Necrotic tissue may be built up. The vessel wall may be structurally weakened. The vessel wall may get damaged by the device. A rupture of the vessel wall may occur. As a consequence, a dissection may occur, i.e. a bleeding out of the vessel wall into surrounding tissue of the vessel.

For instance arteriosclerotic vessel are conventionally difficult to seal off. Arteriosclerotic vessels are brittle, conventional sealing devices have difficulties to find hold or damage the brittle vessel wall, the lumen diameter is already reduced and may be further reduced by members of the known sealing devices protruding into the lumen, etc.

When the applied compression or pressure is too low, i.e. the button device is put in place too loose, pressure damages are avoided. However, a leakage may then occur.

Leakage of blood from the puncture site is not desired, and should be avoided.

In particular repeated puncture, e.g. necessary during intensive treatment periods, of such anatomically sensitive vessels, may lead to damage of the vessel.

WO2006/034114 discloses thin film devices implantable within a human subject for occlusion of an aneurysm or body vessel. The devices are movable from an elongated, collapsed configuration for delivery to a deployed configuration within the body. Such an occlusion device includes a thin film mesh attached to a carrying frame. The carrying frame is moveable between a collapsed configuration and an expanded configuration. The thin film mesh can include a plurality of slits, slots and/or pores that typically vary in degree of openness as the carrying frame moves between the collapsed and the expanded configurations. The occlusion device is transluminally positioned within the blood vessel so that the thin film mesh substantially reduces or completely blocks blood flow to a diseased portion of a blood vessel. However, a puncture itself is needed to deploy this device into the vessel as it is not suitable to be delivered itself through an opening to be closed, US2009/0143815 discloses a device for sealing a puncture opening in a wall of a blood vessel that includes a base frame including a first bi-stable material having a first stable state corresponding to a delivery configuration of the base frame, in which the base frame is retracted to have a relatively smaller overall profile, and a second stable state corresponding to a deployed configuration of the base frame, in which the base frame is extended to have a relatively larger overall profile. The base frame is sized to engage an interior surface of the blood vessel wall when in the deployed configuration. A sealing section is coupled axially as a section to the base frame and includes a second bi-stable material having a first stable state corresponding to an initial configuration of the sealing section, in which the sealing section permits fluid flow, and a second stable state corresponding to a barrier configuration of the sealing section, in which the sealing section prevents fluid flow. The sealing section in the barrier configuration is sized to block fluid flow through the puncture opening when the base frame is in the deployed configuration. However, this device is difficult to deliver as deployment of the base frame is not controllable. Thus, the base frame may expand and engage the vessel wall before the sealing section is correctly positioned. Moreover, this device may migrate along the vessel with too low self expansion pressure of the base frame. The device may also migrate into the vessel wall and damage the latter at too high self expansion force of the base frame. Reliable sealing is thus difficult to achieve with this device. Moreover, a structure as disclosed in US2009/0143815 is traumatic in relation to the vessel wall, in particular at the tissue surrounding the puncture opening.

It is an object of the present invention to provide a novel and inventive device for closure and sealing of a puncture or incision formed in a blood vessel or in other body organs. A further object of the invention is to provide a puncture closure method, in embodiments utilizing the sealing device. The medical arts would benefit from a device that allows for the sealing of blood vessel wall punctures that are created at the termination of a tissue tract that passes through intervening tissues between the vessel wall puncture and a puncture through the skin. It would be preferred if the device was self-securing and small in size so as to be introduced without the need to enlarge the tissue tract beyond the size needed to perform the primary medical procedure.

Hence, an improved medical device or methods for closure of a puncture in a body lumen would be advantageous, and in particular allowing for increased flexibility, and/or patient-friendliness would be advantageous. Advantageously the solution should be atraumatic in relation to the vessel wall, in particular at the tissue surrounding the puncture opening to provide a reliable sealing.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a device, a kit and a method according to the appended patent claims.

According to a first aspect of the invention, a medical device is provided. The medical device is adapted for closure of a puncture in a body lumen, such as a vessel, in a patient. The device comprises an aggregate of a) a support structure having a first shape, which is a temporary delivery shape, for delivery to an interior of the body lumen and to be subsequently subjected to a change of shape to a second shape, which is a tubular shape, when delivered in the body lumen, and b) a substantially fluid tight patch member attached to the support structure, which patch member is at least partly arranged radially outside of the tubular support structure and at least partly arranged towards an inner tissue wall of the body lumen at a site of the puncture of the body lumen when the support structure has the second, tubular shape, such that the puncture is sealed off by the aggregate.

More particularly, a medical device for closing a puncture in a body lumen from the inside thereof, such as a vessel, in a patient, is provided. The device comprises an elongate delivery unit having a distal end; and an aggregate of a support structure having a first shape, which is a temporary delivery shape, for delivery to an interior of the body lumen through the puncture and to be subsequently controllably subjected to a change of shape to a second shape, which is a tubular shape, when delivered in the body lumen, and a patch member attached to the support structure at an intermediate portion between two opposite ends thereof. The distal end of the elongate delivery unit is radially releasably attached to the aggregate at an attachment position intermediate between ends of the patch member and detachable therefrom upon deployment of the aggregate in the body lumen. The patch member is sized and shaped for arranging it towards an inner tissue wall of the body lumen at a site of the puncture of the body lumen and extending over a puncture opening. The delivery unit extends in a direction radially from the aggregate through the opening, such that the puncture is controllably sealed off by the patch when drawing the delivery device in a direction out of the puncture and tightening the patch over the opening before the change of shape of the support structure.

In embodiments the device comprises an elongate delivery unit and a detachment unit detachably, wherein the delivery unit is connected to the aggregate by means of the detachment unit for delivery thereof to the interior of the body lumen, and for detachment of the aggregate upon the delivery to the interior of the body lumen; wherein the elongate delivery unit preferably comprises a delivery catheter, and/or a delivery wire releasably attached to the aggregate.

According to another aspect of the invention, a medical procedure is provided in form of a method. The method is a method of closure of a puncture in a body lumen, such as a vessel, in a patient, by a medical device. The method comprises deploying an aggregate of a support structure and a patch member in the body lumen through a puncture opening in the body lumen at the puncture site, wherein the patch member is a substantially fluid tight patch member attached to the support structure, and wherein the deploying comprises delivering the support structure in a temporary delivery shape to an interior of the body lumen, subsequently subjecting the support structure to a change of shape to a second shape, which is a tubular shape, in the body lumen, and thus arranging the patch member at least partly radially outside of the tubular support structure and at least partly towards an inner tissue wall of the body lumen the site of the puncture of the body lumen when the support structure has the second, tubular shape, and thus permanently sealing off the puncture from inside the body lumen by the aggregate.

According to another aspect, a method of closure of a puncture in a body lumen, such as a vessel, in a patient, by a medical device, is provided. The method comprises providing a patch member arranged on an outside of a tubular support structure and attached to the support structure at an intermediate portion between ends thereof; and an elongate delivery unit having a distal end, wherein the distal end thereof is radially releasably attached to the support structure or the patch member at an intermediate position between ends of the patch member and detachable therefrom upon delivery; wherein the patch member is arranged radially outside of the tubular support structure only at a partial radial section and axial section thereof and arrangeable towards an inner tissue wall of the body lumen at a site of the puncture of the body lumen when the support structure has the second, tubular shape, such that the puncture is sealed off by the patch of the device hold by the support structure in the body lumen at the site.

According to another aspect, a method of closure of a puncture in a body lumen, such as a vessel, in a patient, by a medical device, is provided. The method comprises providing a medical device for closing the puncture in the body lumen from the inside thereof, the method comprising providing an elongate delivery unit having a distal end; and an aggregate of a support structure having a first shape, which is a temporary delivery shape, for delivery to an interior of the body lumen through the puncture and to be subsequently controllably subjected to a change of shape to a second shape, which is a tubular shape, when delivered in the body lumen, and a patch member attached to the support structure at an intermediate portion between two opposite ends thereof; wherein the distal end of the elongate delivery unit is radially releasably attached to the aggregate at an attachment position intermediate between ends of the patch member and detachable therefrom upon deployment of the aggregate in the body lumen; arranging the patch member arranging towards an inner tissue wall of the body lumen at a site of the puncture of the body lumen and extending over a puncture opening, and drawing the delivery device in a direction out of the puncture and tightening the patch thereby controllably sealing off the puncture by the patch; and initiating the change of shape of the support structure for anchoring the aggregate at the puncture site in the vessel; and releasing the delivery device from the aggregate.

In embodiments, the method comprises releasably attaching an elongate delivery unit to the aggregate for delivery thereof to the interior of the body lumen, and detaching the aggregate upon the delivery to the interior of the body lumen; wherein the elongate delivery unit preferably comprises a delivery catheter, and/or a delivery wire releasably attached to the aggregate.

Further embodiments of the invention are defined in the dependent claims, wherein features for the second and subsequent aspects of the invention are as for the first aspect mutatis mutandis.

Some embodiments of the invention provide for safe anchoring of a puncture closing or sealing device with minimal risk of migration in a body lumen. The device is anchored against the vessel wall from the inside thereof. The device does thus not migrate or get washed away from the puncture site. The anchoring may be enhanced, e.g. by anchoring units or members, such as barbs, hooks, protrusions, or other means, such as tissue glue. Also, a protrusion into the puncture opening, e.g. an attachment or detachment device, arranged in the puncture opening remaining there after delivery, avoids a longitudinal migration or wash away. In addition, barbs extending through the patch, even at the puncture opening i.e. without engaging tissue of the body lumen surrounding the puncture opening, provide for a reliable fixation of the patch member to the support structure.

Some embodiments of the invention provide for self removing devices that leave a vessel wall with no remaining device after a certain period of time. This is for instance achieved by bioabsorbable or bioresorbable material. Such material may be applied both in the support structure and/or the patch member.

Some embodiments of the invention provide for a reduced risk of narrowing of the body lumen at the closed or radially sealed off puncture opening. The devices of embodiments have a low profile in radial direction. Some embodiments of the invention thus provide for avoidance of a turbulent flow in the body lumen downstream the puncture site. Thus secondary effects are avoided, such as creation of thrombosis or embolies.

Some embodiments of the invention provide for minimized or eliminated shortcomings of known sealing devices, such a minimized or eliminated risk for damaging brittle lumen tissue, such as vessel tissue, e.g. of the arteria subclavia, or the arteria axillaris. The device and method of embodiments may be applied to body lumen, which conventionally could not be sealed off with known devices.

Some embodiments of the invention avoid a manipulation of the vessel wall. For instance arteriosclerotic vessel walls are advantageously sealed off at puncture sites.

Some embodiments of the invention provide for intraluminal devices, which apply a radially outwardly oriented force, thus minimizing the risk of arterial vessel wall manipulation.

Some embodiments of the invention avoid a squeezing of the vessel wall tissue, thus providing for reduced risk of tissue damage of the vessel wall.

Some embodiments provide for devices that are not substantially extending into lumen. The devices are flat, i.e. have a substantially lesser profile than the diameter of the body lumen in which they are anchored. The devices have a low profile in radial direction. This provides for avoiding turbulent flow at the puncture site when it is sealed off.

Some embodiments of the invention provide for a quick procedure for sealing a puncture site. The devices of embodiments are applied in a short time. There is no need to wait for hardening of chemical sealing agents. Conventional techniques, including the Seldinger technique, may be a basis for introducing embodiments of the device into the body lumen.

Some embodiments of the invention provide for biocompatible devices reducing potential irritation or other implications of the puncture site.

Embodiments of the invention provide for an effective avoidance of bleeding when the puncture site is sealed off by means of devices according to embodiments.

Some embodiments of the invention also provide for devices that apply no double sided compression of a body lumen for sealing a puncture opening.

Embodiments of the invention provide for an effective atraumatic sealing of such puncture. This is for instance provided by a patch contacting tissue wall surrounding the puncture opening. The patch provides at the same time for a reliable sealing of the puncture as it extends over the opening from inside the vessel.

Embodiments provide for a reliable controllability of the sealing process as the patch is arranged in the device to be positioned against the tissue wall surrounding the puncture opening and across the opening before it is anchored in the vessel by the support structure and released from a delivery device. The patch prevents that blood leaves the vessel at the puncture site through the puncture opening and a percutaneous puncture channel. The puncture channel is a tissue tract communicating with the blood vessel.

Embodiments provide for the use of an introducer for the positioning and deployment of the puncture sealing device. An introducer already positioned in the patient for a surgical procedure is left in place for delivery of the puncture sealing device. This is in particular advantageous from a clinical perspective, providing for user acceptance of the device, and cost efficiency as the introducer is useable even during closing of the puncture site.

Embodiments provide for a device that is self-securing and small in size, and to be introduced without the need to enlarge the tissue tract (herein also called puncture channel) beyond the size needed to perform a primary medical procedure.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
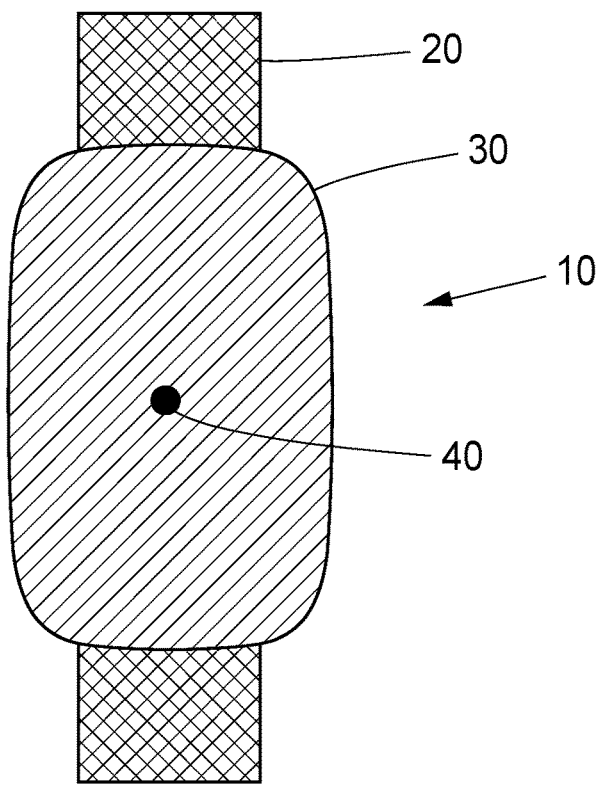
FIG. 1 is a view from above showing a schematic illustration of an embodiment of an aggregate for sealing a puncture.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on embodiments of the present invention applicable to a blood vessel and in particular to a peripheral blood vessel. However, it will be appreciated that the invention is not limited to this application but may be applied to many other punctured blood vessels or body lumen, including for example those of the urinary tract, or the gastrointestinal tract, including bile ducts or liver vessels or ducts, or of kidney vessels or ducts, or the central nervous system, etc. However, embodiments do not include devices for treatment of defects in intra cardiac structures, such as atrial appendices, atrial or ventricular septal defects, as these are not body lumina within the meaning of this application.

Figure 2:
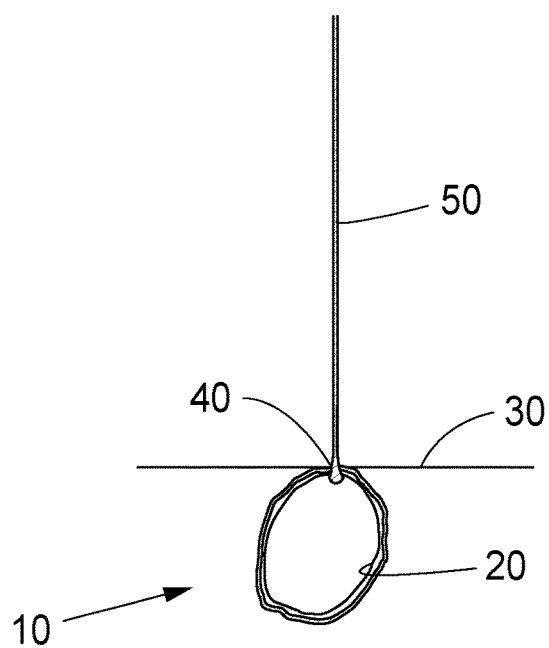
FIG. 2 is a frontal view showing a schematic illustration of the aggregate of FIG. 1 attached to a delivery wire.
Figure 3A:
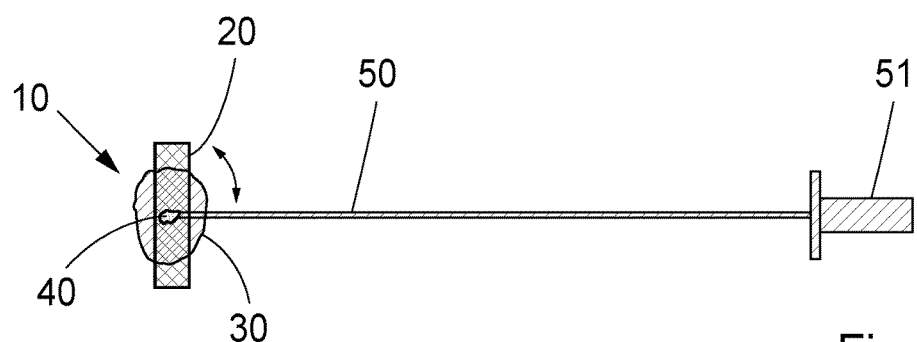
FIG. 3A is a lateral view of the aggregate of FIG. 2.
Figure 3B:
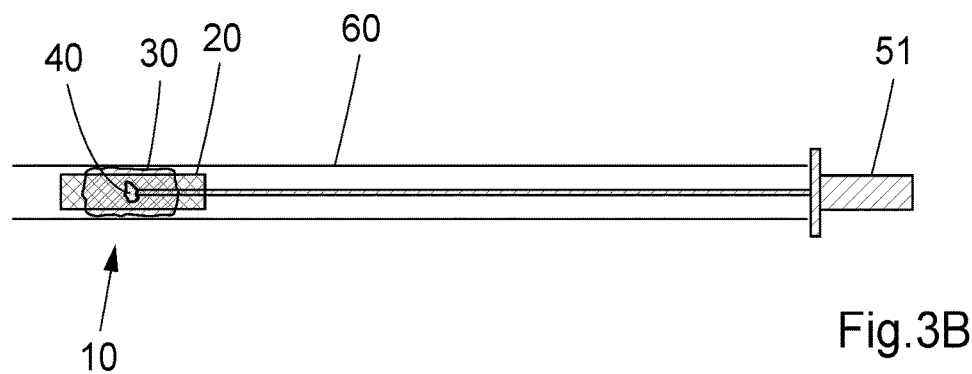
FIG. 3B is a lateral cross sectional view of the aggregate of FIG. 2 in a delivery catheter.

Now turning to the FIGS. 1-3 an embodiment of the invention is described in more detail. FIG. 1 is a view from above showing a schematic illustration of an embodiment of an aggregate 10 of a medical device for closure of a puncture in a body lumen, such as a vessel, in a patient. FIG. 2 is a frontal view showing a schematic illustration of the aggregate 10 of FIG. 1 attached to a delivery wire. FIG. 3A is a lateral view of the aggregate 10 of FIG. 2. FIG. 3B is a lateral cross sectional view of the aggregate 10 of FIG. 2 in a delivery catheter 60.

The medical sealing device is adapted for delivery through the puncture site itself, into to the interior of the body lumen, for deployment therein.

The medical device for closure or sealing of the puncture in the body lumen comprises the aggregate 10, which comprises a support structure 20 and a patch member 30.

The support structure 20 has a first shape, which is a temporary delivery shape, for delivery to an interior of the body lumen. Here, the first shape is a radially compressed shape and the support structure 20 is a collapsible tubular structure.

The tubular support structure 20 is expandable from the first shape, when subsequently subjected to a change of shape, to a second shape. The second shape is a tubular shape. The aggregate is adapted to change shape from the first shape to the second shape when delivered in the body lumen. The aggregate is deployed in the body lumen, and engages the lumen wall of the body lumen for a secure anchoring or fixation therein, avoiding a migration in longitudinal direction of the device along the lumen.

The tubular shape of the support structure 20 may be a net-like shape formed of closed loops, or a mesh shape of a braided, woven or knitted fabric. The support structure may be produced by suitably laser cutting a solid tube to provide a strut structure. The support structure may be provided in form of a stent like tubular member. The support structure may be self expandable. Alternatively, or in addition, the support structure may be expandable by expanding units, such as an inflatable balloon. When self-expandable, expansion may be controllable as described below. Expansion by expanding units renders the change of shape controllable as such.

The anchoring may be enhanced, e.g. by anchoring members, such as barbs, hooks, protrusions, or other means, such as tissue glue comprised in the aggregate 10. Either, or both, the support structure 20 and the patch member 30 may comprise such radially outwardly arranged anchoring members. The anchoring members engage with the wall tissue of the body lumen, and may protrude into the surrounding tissue. Anchoring members may also protrude from the support structure through the patch member at the puncture opening, thus keeping it reliably in place in addition to the radially outwardly oriented anchoring force thereof.

In the embodiment, the support structure 20 is made of a resilient material and is self expanding, and wherein the first shape is tubular of a smaller diameter than the second, tubular shape. A restriction unit may be provided for restricting resiliency based expansion until the patch is positioned over the puncture opening.

Alternatively, or in addition, the support structure 20 may be made of shape memory material, such as a shape memory polymer, or a shape memory alloy, such as NiTinol. A restriction unit may be provided for restricting shape memory based expansion until the patch is positioned over the puncture opening.

The patch member 30 is substantially fluid tight. This may be implemented by providing the patch member 30 of a suitable fabric. Alternatively, the patch member 30 may be provided in form of a solid membrane material.

The patch member is made of a tissue friendly material. The patch member is not necessarily 100% fluid tight, depending on the application. For instance, blood coagulation may occur upon deployment in the patch member providing for a sufficient sealing to stop a bleeding out of the puncture.

The patch member is semi rigid. The patch member is thus adapted to get into apposition with the tissue wall of the body lumen and conform to the structure thereof. This provides for easy deployment and a reliable sealing, e.g. upon retracting the delivery wire.

The patch member may even be stretched or partly drawn into the puncture channel, like a thick paper tissue.

The patch member is atraumatically held into position over the puncture opening by an elongate delivery device attached to the sealing device within the surface covered by the patch member. Thus the puncture member is fixatable over the puncture opening by drawing the delivery device in a direction out of the patient.

The support structure may then be fully deployed to a tubular shape in the body lumen, Such release of the support structure to the tubular shape may be initiated by active user operated and controlled means, e.g. a tether, electrically, etc Alternatively, the release of the support structure to the tubular shape may be initiated automatically, e.g. after a certain time in contact with body fluids. The time is suitably chosen such that reliable positioning of the patch member is provideable for sealing the puncture before the change of shape is initiated. Alternatively, or in addition, the change of shape may be provided partly upon release in the body vessel, and then finalized to the fully tubular shape upon user operation or automatically after a suitable time.

Upon final deployment of the support structure, the device is released from the delivery device and left in-situ.

The patch member 30 is attached to the support structure 20. Attachment is made on at least one defined point of the support structure 20, as illustrated at attachment point 40 for a delivery device in the Figures.

The patch member 30 is arranged radially outside of the tubular support structure along a portion of the tubular structure, when the support structure has its second shape. The patch member is adapted to fit over the puncture opening 110, thus being supported by the support structure providing a fluid tight sealing of a puncture site 100. The patch member is thus at least partly arranged towards an inner tissue wall of the body lumen at a site of the puncture of the body lumen when the support structure has the second, tubular shape, such that the puncture is sealed off by the aggregate 10.

The patch member itself is non-tubular and has a longitudinal extension shorter than a length of the support structure in the expanded diameter. Further, the patch member has an extension shorter than a circumference of the support structure in the expanded diameter at the puncture site. The patch member is thus arrangeable radially outside of the tubular support structure only at a partial radial section and axial section thereof. This has the advantage that migration along the body vessel is prevented, as anchoring is provided by the support structure outside of the patch member when in contact with wall tissue, even in an axial portion along its length at the puncture opening.

In embodiments, the patch is not a so called "thin film" (only several microns thick). A thin film would not be suitable for attachment of a delivery unit due to lacking structural strength.

The patch member has in some implementations for instance a thickness of 0.1 mm to 1 mm, depending on the application site of the device. The patch thickness should not substantially reduce the channel cross section of the body lumen when the device is implanted therein.

As can be seen in FIG. 1 and FIG. 2, the patch member may be attached to the support structure at a single location only. Preferably, this is a central location where also the attachment unit 40 is located.

The periphery of the patch member is thus not attached to the support member. In this manner, an expansion of the support structure is not hindered by the attached patch member.

The conformable patch member thus conforms to the inner of the tissue wall of the body vessel. Upon the change of shape it is anchored in that position from the inside of the vessel by the support structure.

As shown in FIG. 1, the elongate delivery unit is a delivery wire 50 releasably attached to the device 10, at a position between two opposite ends of the device, at a distal end of the delivery wire. 50. The delivery wire 50 is attached to the device 10 at an area covered by the patch member 30. Preferably, the delivery wire is attached to the device centrally at the patch member. This provides for a symmetrical arrangement. Alternatively, asymmetrical attachment arrangements may be provided, e.g. depending on requirements of the puncture site to be sealed off.

The delivery wire is sufficiently rigid to push the sealing devices through a catheter and/or an introducer to the body vessel through the puncture channel.

As shown in FIG. 1, the delivery wire 50 is going through the patch member 30 and is releasably attached to the support structure. Alternatively, or in addition, the delivery wire may be attached to the patch member, which then in turn is attached to the support member.

The delivery device is retractable through the channel of the puncture out of the patient. This retraction is done after detachment when the aggregate of patch and support structure is deployed and seals the puncture from inside the body lumen.

The elongate delivery unit may further comprise a separate delivery catheter insertable through an introducer positioned in the puncture. The catheter is not attached to the aggregate, but merely facilitates delivery thereof.

In embodiments, the device's support structure 20 has a diameter in the second, tubular shape that is, at least slightly, larger than a diameter of the body lumen at the puncture site. In this manner the support structure 20 is devised to anchor the aggregate 10 in an interior of a body lumen 210 at the puncture site 100. The patch member 30 is arranged to extend over the puncture opening 110 in the body lumen 210 at the puncture site 100 for the closure of the puncture. Also, in this manner, the expanded shape of the aggregate 10, because it has a diameter larger than that of the lumen, will somewhat expand the wall of the body lumen 210 radially outwards. In this manner, the aggregate is radially outwardly oriented in relation to the natural diameter of the inner body lumen—it is "recessed", pushing the lumen wall outside. This improves anchoring on the one hand, but also provides a large opening of the body lumen at the puncture site upon sealing with the aggregate 10.

As shown in FIG. 2, the device further comprises an elongate delivery unit and an attachment unit 40 for temporary attaching the delivery unit to the aggregate 10. The delivery unit may comprise a delivery wire 50 and a delivery catheter sheath 60, as described above with reference to FIG. 1. The delivery unit is elongate. At its distal end, the delivery unit is connected to the aggregate 10 by means of the attachment unit 40, which might comprise a detachment unit for controlled release. When assembled, the aggregate is ready for delivery to the interior of the body lumen. Detachment of the aggregate upon the delivery to the interior of the body lumen may be made in various ways, such as by releasing a threaded attachment, activating a detachment means, such as a thermally, electrically, chemically initiated detachment, etc.

In another example, the proximal portion of the delivery wire 50 may be cut off. This is preferably made as close to the distal attachment position as possible.

In another examples, the delivery device may include a gripper or forceps like tool at the end of the delivery device. The attachment unit may then be shaped matingly to allow for a reliable engagement with the tool. The attachment unit may be spherically shaped, allowing for the pivoted movement during delivery. When the tool is locked, e.g. by a sleeve put over the forceps or gripper, a flexible deployment is provided with a reliable delivery without the risk of unintentionally loosing the device into the body lumen. Detachment may be controlled from the outside of the patient, e.g. by withdrawing the locking sleeve and then opening the gripper or forceps.

In some embodiments, the delivery wire 50 is connected to the aggregate 10 at the attachment unit 40 by releasably threaded attachment. The detachment unit is a threaded unit such that the aggregate is detachable from the delivery unit by unscrewing the delivery wire 50 from the aggregate 10. This may leave a protruding attachment unit 40 in the puncture opening, as will be seen below, which advantageously contributes to the anchoring of the aggregate 10 at the puncture site 100 for a reliable sealing. As shown in the figures, the thread is arranged in a radial direction outward from the support structure. The radial direction is substantially perpendicular to a longitudinal axis of the sealing device. As e.g. shown in FIG. 7H, the detachment unit may extend radially from the support structure for being received in the puncture opening, and also in the puncture channel.

In embodiments, the support structure 20 and/or the patch member 30 are made of a biodegradable and/or bioresorbable material.

The support structure 20 is for instance made of a polymer material, or stainless steel, a titanium alloy or a magnesium alloy. The support structure 20 may be provided in form of a wire structure.

The patch member 30 is for instance made of a biopolymer, or a metal alloy like the aforementioned. The patch member 30 is provided as a fabric. In other examples, the patch member 30 may be provided additionally or alternatively as a solid membrane. The patch member is semi rigid. The patch member is thus adapted to get into apposition with the tissue wall of the body lumen and to conform to the structure thereof.

The material has a suitable degradation rate under physiological conditions in order to make the aggregate become degraded or absorbed when the puncture has healed completely.

Suitable biocompatible polymer materials are e.g. described in published US patent application US 2008/0095823, or PCT application PCT/EP2006/062400, which are incorporated by reference herein in their entirety for all purposes. Biocompatible polymer materials comprise polymer compositions with controlled degradation rates, such as polyhydroxyalkanoate.

In some embodiments, the support structure 20 and/or the patch member 30 comprise a pharmaceutical agent.

The pharmaceutical agent is for instance adapted to prohibit a thickening of a wall of the body lumen, such as any one in the group of cyclosporine, taxiferol, rapamycin and tacrolimus. Thus, a reduction of the lumen diameter is further prevented and a flow through the lumen maintained, even during a healing phase of the puncture.

The pharmaceutical agent may comprise an anti-coagulation agent, such as Heparin or an anti-thrombotic agent. Thus, the passage of the lumen is effectively kept open, and thrombosis at or downstream the puncture site is prevented.

The patch member 30 may comprise a fibrosis promoting agent. This provides for an accelerated healing process for finalizing the final, biological sealing of the puncture quicker. The patch member 30 may comprise a scar reducing agent. In this manner, scars at the puncture site 100 are effectively reduced, which is of interest for cosmetic treatment. A fibrosis promoting agent or scar reducing agent is preferably arranged at the patch member 30 such that it is oriented towards the vessel wall, more preferably towards the puncture opening. This may be implemented by having the agent as a coating or a surface layer on a side of the patch member 30 oriented in this manner when the aggregate 10 is deployed.

The pharmaceutical agent may include any one in the group of an endothelia growth promoting agent, such as Endothelium Growth Factor. This provides for an improved growth of a thin layer of endothelia over the aggregate in the inner of the body lumen. This layer of endothelia further supports sealing of the puncture opening. Once a layer of endothelia has built up, biodegradation of the aggregate may be initiated, e.g. controlled by a delayed biodegradation after deployment.

The pharmaceutical agent may comprise an anti-pathogenic agent, or an anti-infectious agent, such as Nitric Oxide. This provides for a more reliable healing of the puncture.

Any of the aforementioned agents may be present in an arbitrary suitable combination at the aggregate 10.

The sealing device of embodiments comprises at least one element to activate or de-activate the change of shape, such as a connection element of the support structure that is arranged such that a connection formed by the connection element between a first and second part of the support element. The connection element is configured to break when the connection element is subjected to a specific external influence, such as stress, temperature, moisture, biodegration, or absorption. Such connection elements are in detail describe in PCT/EP2006/062403, which is incorporated by reference herein in its entirety for all purposes. Thus, the change of shape and engagement with the tissue structure is controllable.

The sealing device of certain embodiments has a support structure 20 that is bistable between a first state of minimum energy and a second state of minimum energy, whereby the change of shape, in use, is obtained as a movement between the first state of minimum energy and the second state of minimum energy. Bistable devices, however for different application than sealing devices, are for instance disclosed in US patent application US 2002/0142119 or US patent application US 2004/0193247, which are incorporated by reference herein in their entirety for all purposes.

The body lumen is in specific embodiments a peripheral blood vessel, and the puncture is a percutaneous puncture of the blood vessel. More particularly, the blood vessel is an arterial, high blood pressure, blood vessel to be sealed off at a puncture site, preferably after a finished surgical procedure involving the use of intra body access through the puncture, e.g. via an introducer unit. The device is thus in specific embodiments an intravascular closure device. More particularly, the puncture is a blood vessel wall puncture at the termination of a tissue tract that passes through intervening tissues between the vessel wall puncture and a puncture through the skin.

Figure 7A:
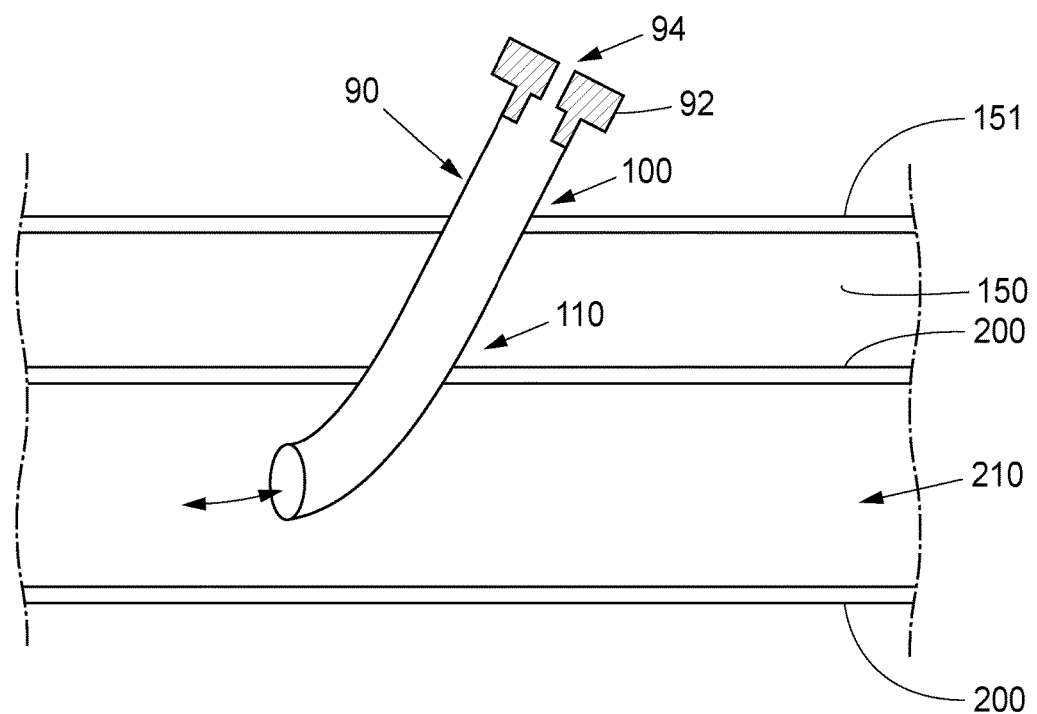
FIGS. 7A-7J are schematic views illustrating a method of sealing a puncture site by means of a sealing device of the type shown in FIGS. 1 and 2.
Figure 7B:
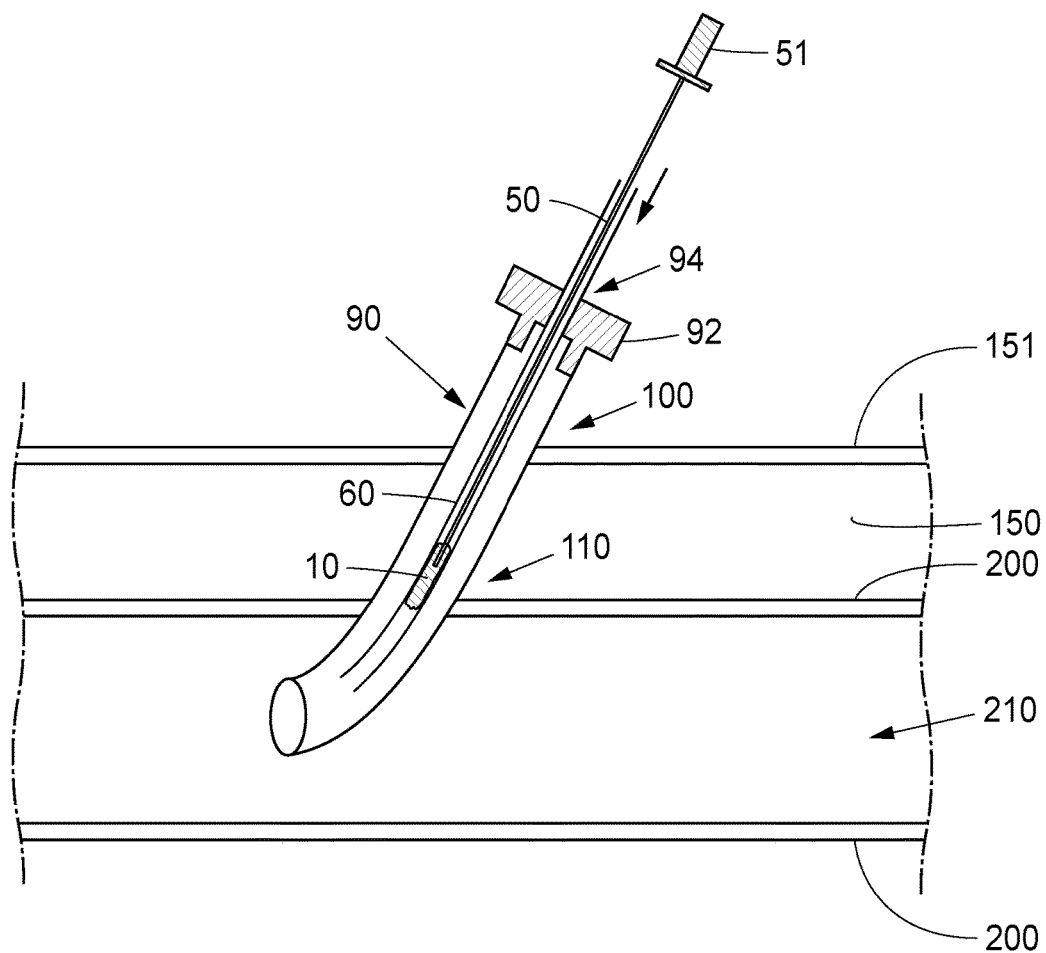
Figure 7C:
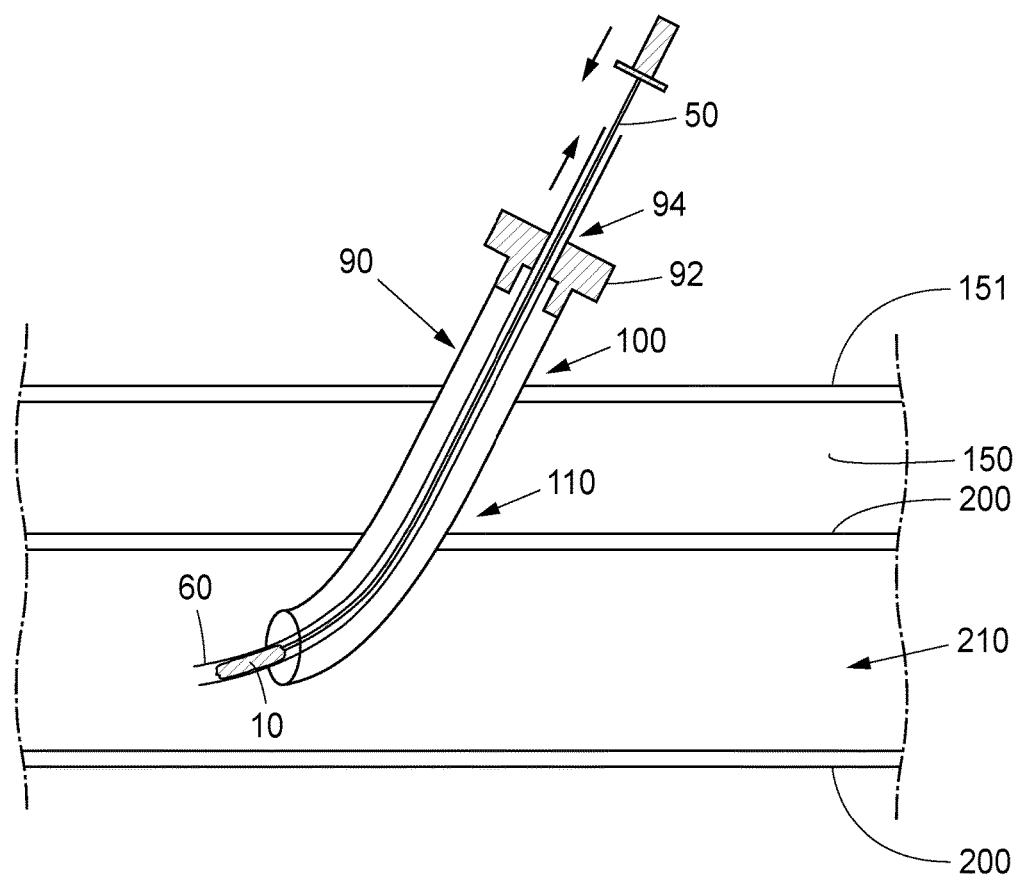
Figure 7D:
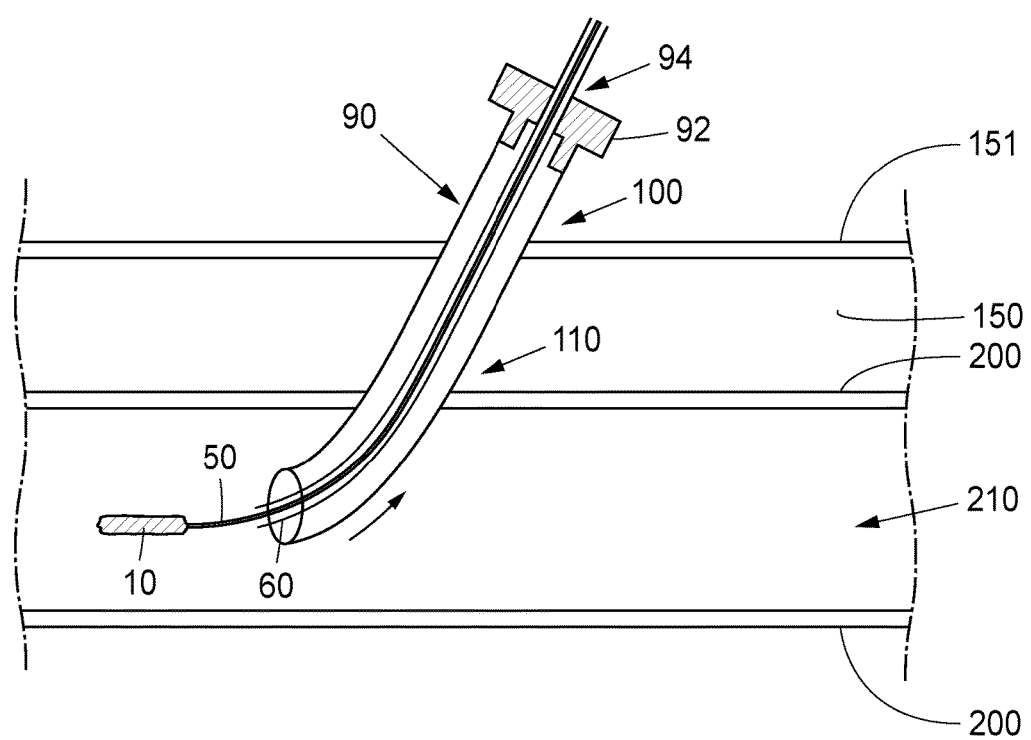
Figure 7E:
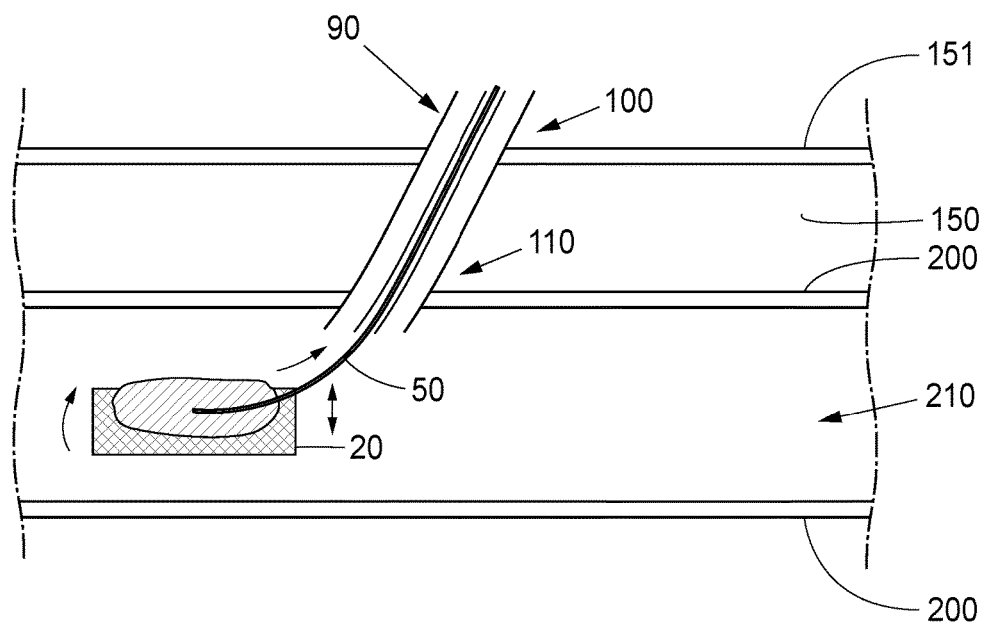
Figure 7F:
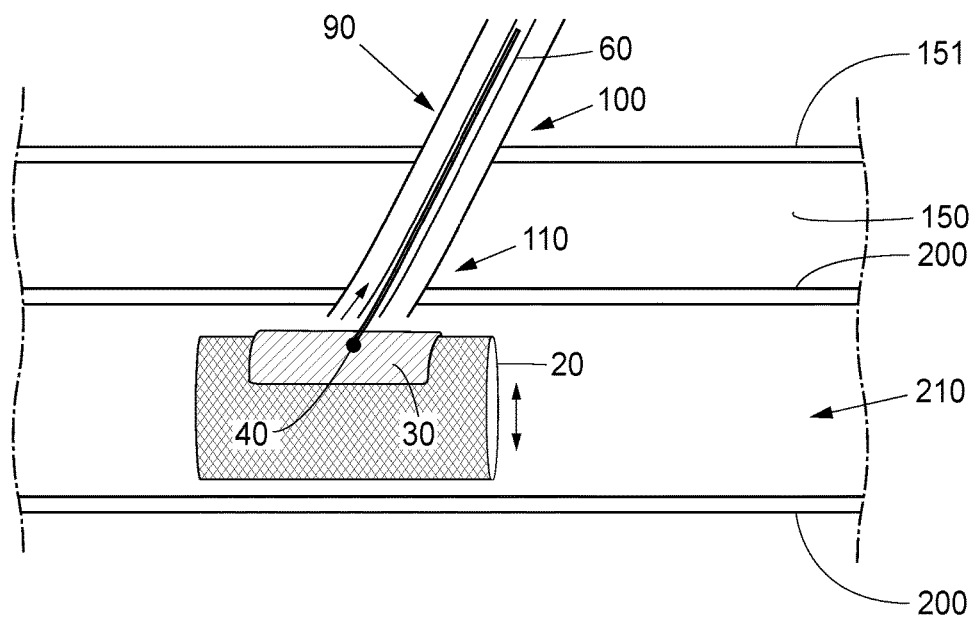
Figure 7G:
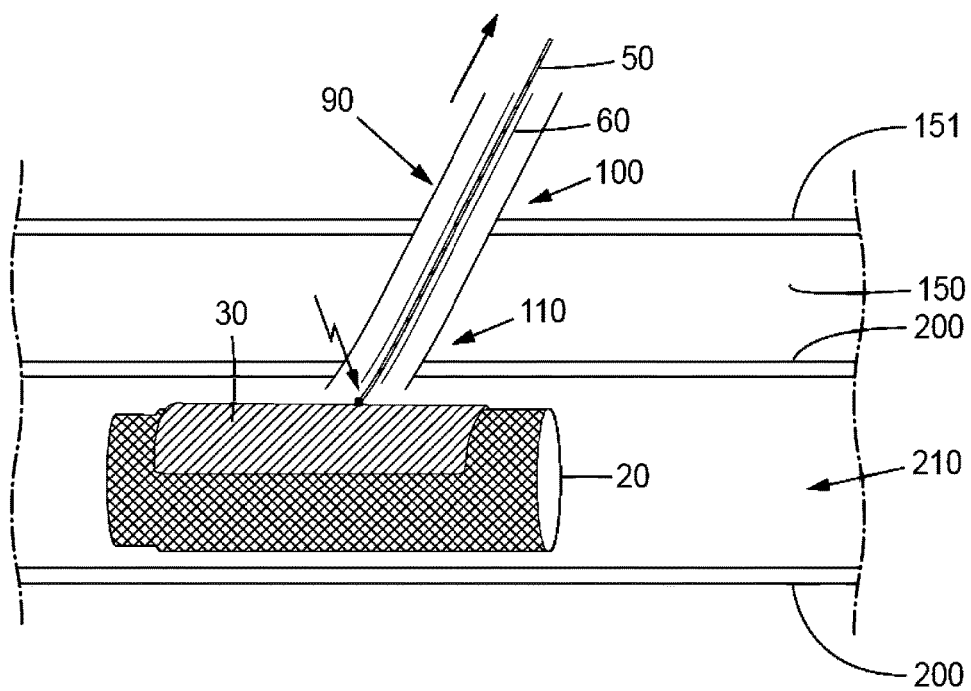
Figure 7H:
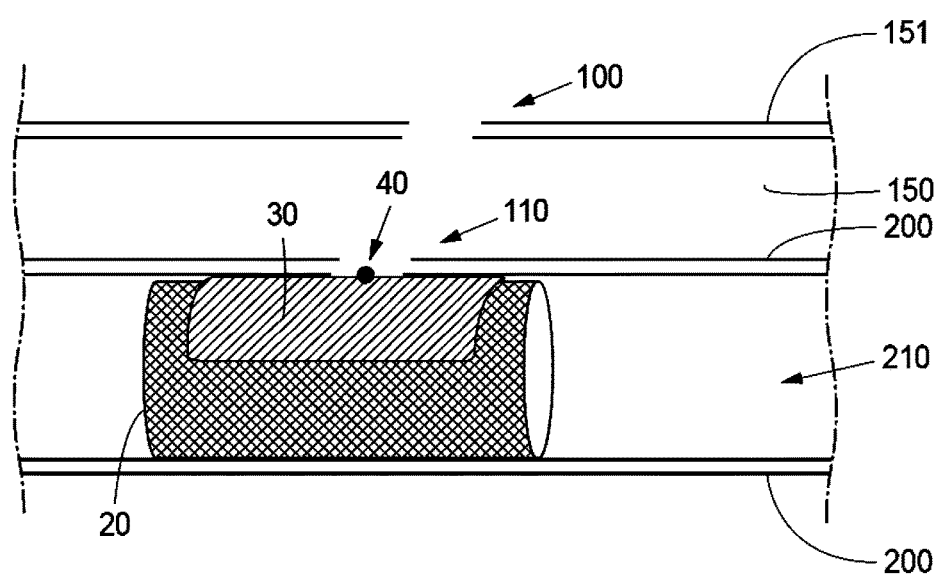

As for instance can be seen in FIG. 7H, the attachment unit 40 or detachment unit is arranged at the aggregate 10 such that the tubular support structure 20 is arranged symmetrically in longitudinal direction in the body lumen 210 in relation to the puncture site.

A kit comprises the afore described sealing device and an introducer sheath 90.

FIGS. 7A-7J are schematic views illustrating a method of sealing a puncture site by means of a sealing device of the type shown in FIGS. 1 and 2.

In the method an aggregate 10 of a support structure 20 and a patch member 30 are deployed in the body lumen 210 through a puncture opening 110 in the body lumen 210 at the puncture site 100.

An introducer 90 having a port 94 at an exterior cap at a proximal end 92 is shown inserted in a puncture in FIG. 7A. The distal end of the introducer is in communication with the proximal end 92, and inserted through the skin surface 151, the surrounding tissue 45, and the body lumen wall tissue 200.

To gain access to the body lumen, the Seldinger technique is employed. This involves placing a small gauge hollow needle through the skin at about a 30 degree angle to intersect the desired lumen. The needle is known to have punctured a blood vessel wall when blood exits the needle at the proximal end. A guidewire is inserted through the needle into the vessel and the needle is removed. A dilator with a lumen sized to fit the guidewire has a leading tapered end and an outside diameter sized to fit closely in an introducer sheath 90 placed over it. The introducer sheath size 90 is selected to accommodate the catheters anticipated to be used in the procedure. The introducer sheath 90 and tapered dilator are advanced together over the guidewire through the skin and into the vessel. The dilator and guidewire are then removed, since the vascular pathway from outside the body through the sheath and into the vessel have been established. A self sealing stretchable valve may be provided at the proximal end 92 of the introducer sheath 90, which minimizes blood loss from the introducer sheath during the procedure.

When a procedure performed via this port in the patient's body is finished, the puncture has to be sealed.

According to embodiments of the sealing method, the support structure 20 is delivered in a temporary delivery shape to the interior of the body lumen 210 through the introducer 90, as illustrated in FIG. 7B.

In FIG. 7C, the aggregate 10 is advanced through the introducer 90, together with the catheter 60 and the delivery wire 50. 18. The aggregate 10 is attached to the delivery unit by screwing the delivery wire 50 to connect it to the aggregate 10 by releasably threaded attachment. Later on, the aggregate 10 is detached from the delivery unit by unscrewing the delivery wire 50 from the aggregate 10, as described further below.

Then, the delivery catheter 60 is partly withdrawn, releasing the aggregate into the body lumen, while still attached to the delivery wire 50 at the attachment unit 40, as illustrated in FIG. 7D. Further, the introducer and the delivery catheter are further withdrawn, such as illustrated in FIG. 7E. The delivery wire 50 is withdrawn, such that the attachment point 40 is drawn to the puncture site 110. The aggregate 10 is thus suitably rotated and pivoted in relation to the delivery wire 40, as illustrated in FIGS. 7E and 7F. The patch member is automatically aligned centrally in relation to the puncture opening 110. The correct pivotal movement may be ensured by a rotation of the guide wire 50.

The elongate delivery unit is thus radially releasably attached to the aggregate. Attachment may be made via a hinge, swivel or pivoting means at the attachment point to the aggregate.

In this manner, the tightness of the body fluid leaking out of the puncture is controlled by the patch drawn against the opening.

At the same time, the support structure 20 is controllably subjected to a change of shape to a second shape, which is a tubular shape, in the body lumen. This change of shape may for instance be provided by resiliently expanding the support structure 20 when it is released out a protective sheath, restricting the support structure 20 from expanding during delivery. Alternatively, or in addition, the support structure 20 may change its shape based on a shape memory effect, e.g. initiated by the body temperature of the fluid in the body lumen 210. The change of shape is illustrated in FIGS. 7D-7H.

The change of shape may be activated or de-activated by means of at least one connection element of the support structure that is arranged such that a connection formed by the connection element between a first and second part of the support element is configured to break when the connection element is subjected to a specific external influence, such as stress, temperature, moisture, biodegradation, or absorption.

The change of shape may be obtained by transforming the support structure from a bistable first state of minimum energy in the first shape to a second state of minimum energy in the second shape, by a movement between the first state of minimum energy and the second state of minimum energy.

The illustrated method comprises expanding the support structure to a diameter in the second, tubular shape that is larger than a diameter of the body lumen at the puncture site. Further, the support structure is anchored in the interior of the body lumen at the puncture site, whereby the patch member is arranged to extend over the puncture opening in the body lumen at the puncture site for the closure of the puncture. The anchoring may be enhanced, e.g. by anchoring members, such as barbs, hooks, protrusions, or other means, such as tissue glue.

The method may comprise self expanding the support structure 20 in the body lumen 210 upon delivery therein. Preferably this is done when the patch is suitably positioned and sealing tightness is achieved.

Thus, the support structure upon the change of shape is holding the aggregate in the body lumen at the puncture site extending over the patch member radially between the tissue wall and the support structure in the second, tubular shape. The patch member is overlappingly contacting the inner tissue wall of the body lumen and is extending over the puncture opening.

The patch member may be made to partly extend into the puncture channel at the puncture opening. This may provide for a particular quick and reliable sealing of the puncture.

Hence, the puncture opening is initially closed with the patch member before the support member changes shape to the tubular shape.

The method comprises retracting the delivery device upon detaching from the device through a channel of the puncture out of the patient.

Hence, the support structure upon the change of shape is holding the aggregate in the body lumen at the puncture site extending over the patch member radially between the tissue wall and the support structure in the second, tubular shape.

The patch member is overlappingly contacting the inner tissue wall of the body lumen and is extending over the puncture opening.

The method may comprise drawing the patch member partly into the tissue tract from the puncture opening.

In certain medical procedures, the puncture channel may additionally be closed by injecting or inserting a clotting induction agent such as collagen that encourages clotting in the puncture channel.

The method may comprise initially closing the puncture opening with the patch member before the support member changes shape to the tubular shape.

The method may comprise retracting the delivery device upon detaching from the device through a channel of the puncture out of the patient.

The patch member is thus arranged radially outside of the tubular support structure, towards an inner of tissue wall 200 of the body lumen 210 at the puncture site 100 of the body lumen when the support structure has the second, tubular shape, and thus the aggregate 10 is permanently sealing off the puncture from inside the body lumen by the aggregate.

The sealing effect of the aggregate 10 is supporting or enhanced by a physiological pressure of a body fluid in the body lumen onto the patch member, pressing it against the tissue wall 200 of the body lumen 210.

Thus, an intra-luminal leakage tight sealing of the puncture is obtained.

The method may comprise delivering a pharmaceutical agent, as those described above, from the aggregate 10 at the puncture site to the body lumen 210.

The elongate delivery unit releasably attached to the aggregate 10 for delivery thereof to the interior of the body lumen 210 is then detached from the aggregate, leaving the aggregate securely in place, as illustrated in FIG. 7H.

The puncture channel through the vessel wall 200 and the surrounding tissue, as well as the outer skin will heal, as illustrated in FIG. 7H.

The method may further comprise biodegrading the aggregate 10 when deployed in the body lumen at a degradation rate under physiological conditions. When the aggregate 10 is made of a biodegradable or bioresorbable material, the puncture site will be reliably sealed, without any remainders of the aggregate 10 at the previous puncture site, as shown in FIG. 7J. The aggregate 10 may be provided to start to biodegrade when endothelium has covered the aggregate installed in the body lumen.

The method and device facilitate re-puncturing the body-lumen 210 at the puncture site 100 by re-enforcing the lumen wall 210 of the body lumen 210 and supporting a patency of body lumen.

Both the support structure 20 and the patch member 30 are penetratable by a needle tip when a new puncture of the body lumen 210 is desired after sealing of the puncture site 100.

When the aggregate 10 is absorbed or degraded, the previous puncture site is also available for a new puncture.

In embodiments, the body lumen is an arterial blood vessel. In particular, the body lumen is a peripheral blood vessel, and the puncture is a percutaneous puncture of the body vessel, wherein the device is an intravascular closure or sealing device for a vascular puncture.

The peripheral blood vessel is in particular an arteria subclavia, or an arteria axillaris of the patient. The puncture site is in particular in a region of a clavicle of the patient.

In embodiments, the body lumen is the patient's aorta, including the ascendant or descendent aorta, or branch vessel of the aorta.

Figure 4:
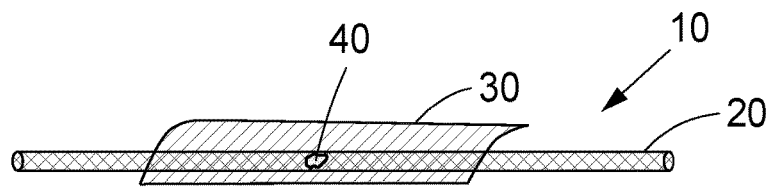
FIG. 4 is a view from above showing a schematic illustration of anther embodiment of an aggregate for sealing a puncture in a first shape.

A further embodiment of the device and method of the invention is illustrated in FIGS. 4-6 and 8A-8D. FIG. 4 is a view from above showing a schematic illustration of another embodiment of an aggregate 10 for sealing a puncture, in a first shape. The first shape is in this embodiment an elongate shape, which is substantially straight.

Figure 5:
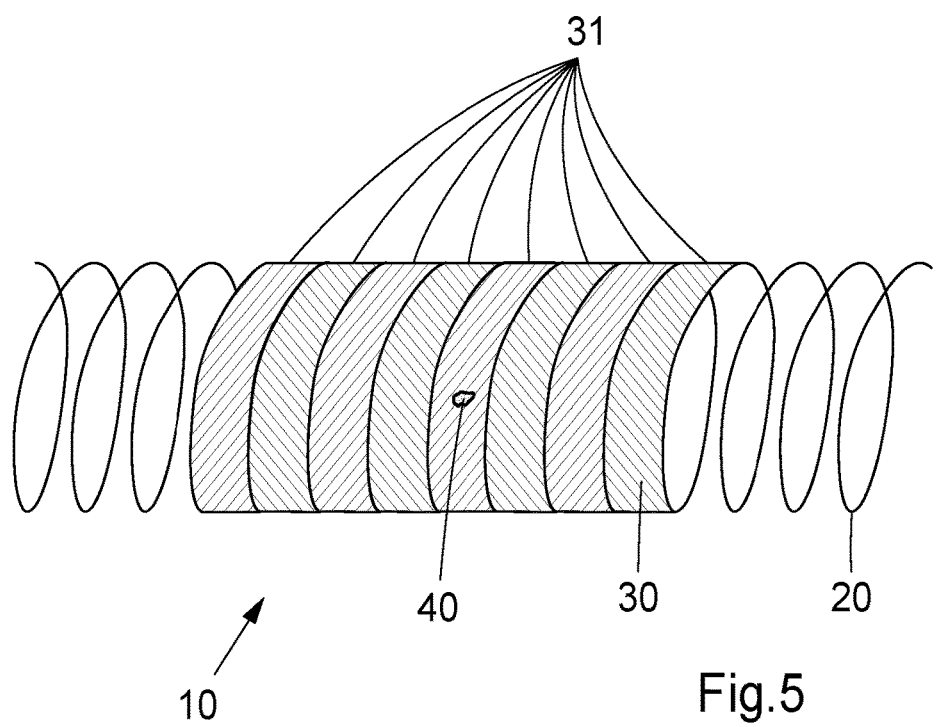
FIG. 5 is a lateral view showing a schematic illustration of the embodiment of FIG. 4 in a second shape.

The support structure is made of a resilient material and/or a shape memory material, such as a shape memory polymer or a shape memory metal or alloy thereof. The second, tubular shape is a helically coiled shape of the support structure 20. FIG. 5 is a lateral view showing a schematic illustration of the embodiment of FIG. 4 in the second shape.

Figure 6:
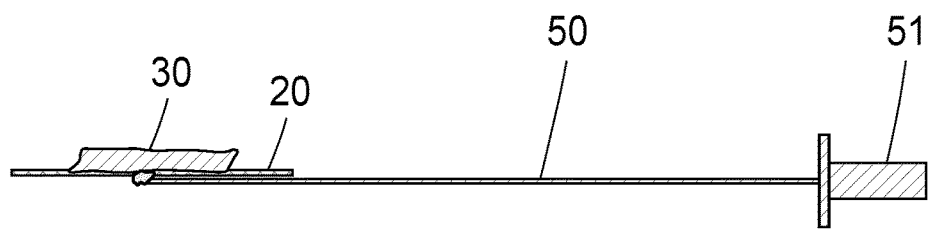
FIG. 6 is a cross sectional view of the aggregate of FIG. 4 in its first shape attached to a delivery device.

FIG. 6 is a cross sectional view of the aggregate 10 of FIG. 4 in its first shape attached to a delivery wire 50 in its first shape. Like the above described embodiments, the aggregate 10 may be restricted in this first shape by a catheter sheath.

The patch member 30 is an elongate strip of fluid tight material. The patch member is attached to the support structure 30 along a portion of its length. The length of the patch member is at the most equal to the entire length of the support structure 30.

The patch member 30 may be put like a sock over the elongate support structure 20.

The patch member extends like a collar from the support structure.

The patch member may have a plurality of patch sub units (not shown) arranged along the length of the elongate support member. The patch units, e.g. of fabric, are arranged at a distance from each other such that they are arranged in the same radial direction at the attachment point of the delivery device distal end at the tubular support structure in the second, tubular coiled shape.

When the support structure is in its second shape, the patch member is arranged overlapping itself to provide a fluid tight structure. The patch member may overlap on the inside or the outside of the tubular structure. In this manner, a fluid tight structure of overlapping strips 31 at each turn or winding of the helical coil making up the tubular structure, is provided, as illustrated in FIG. 5.

The minimum length of patch member is such that it extends along so many windings that longitudinally extend over the puncture opening and a bit further, in order to provide a reliable sealing thereof.

The width of the patch member 30 is determined by the pitch of the helical coil, and is larger than the distance between two windings of the latter. Thus the distance between the windings is bridged, and by the overlapping sections of adjacent windings, a continuous fluid tight structure is provided along the tubular support structure.

The width may also vary along the length of the patch member 30. For instance the end section may narrow down. The middle section may have a larger width to provide a larger overlap. The longitudinal width variation may be chosen suitably depending on various parameters, such as the anatomical structure of the body lumen at the puncture site, the pressure of a body fluid at the puncture site, etc.

FIGS. 8A-8D are schematic views illustrating a method of sealing a puncture site by means of a sealing device of the type shown in FIGS. 4 to 6.

Introduction of the delivery assembly of FIG. 6 into the body lumen at the puncture site is made similar as described above with reference to FIGS. 7A-7E and is not repeated to avoid redundancy.

The method comprises transforming the support structure 20 of FIG. 4-6 from the first elongate delivery shape, to the second, tubular shape, which is a helically coiled shape of the support structure, wherein the transforming is based on an elasticity or shape memory effect of the support structure 20.

Figure 8A:
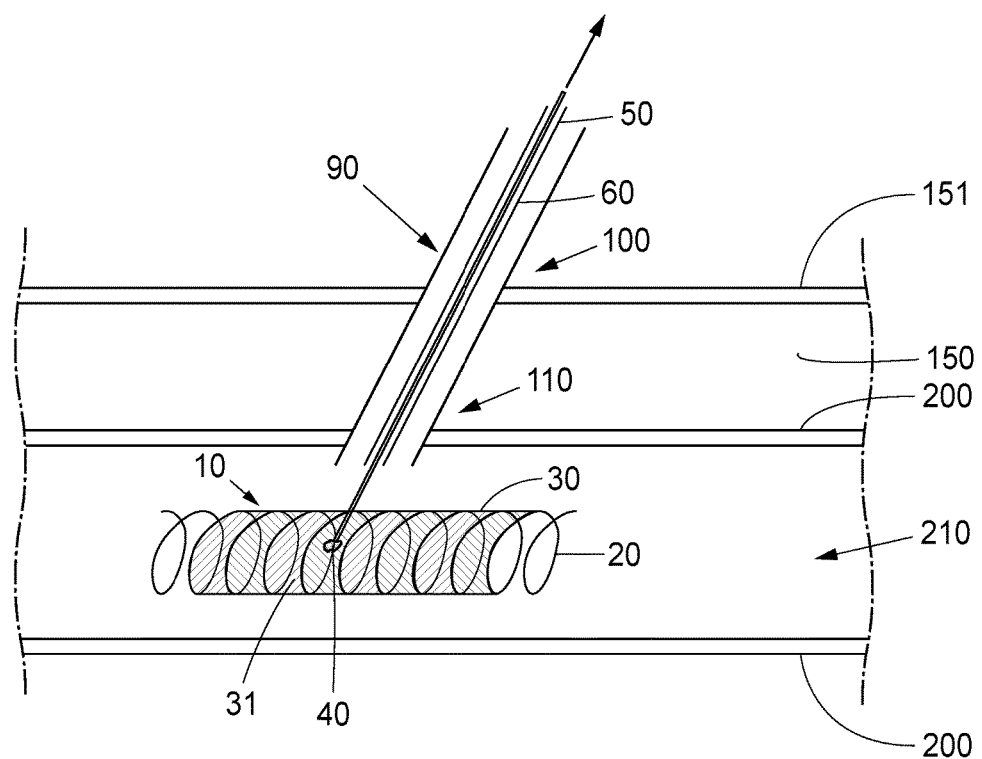
FIGS. 8A-8D are schematic views illustrating a method of sealing a puncture site by means of a sealing device of the type shown in FIGS. 4 and 5.
Figure 8B:
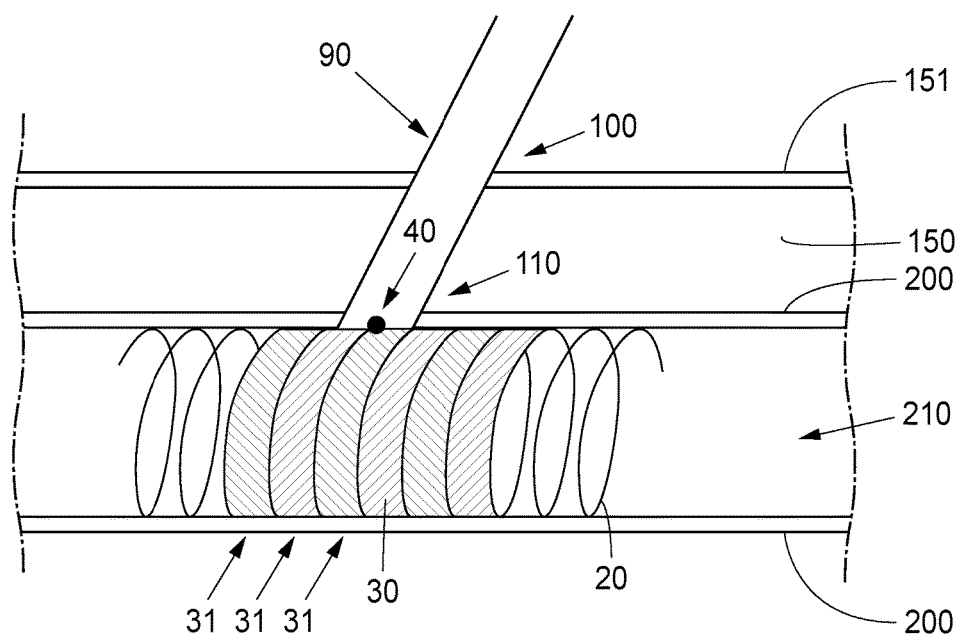

FIG. 8A shows the aggregate 10 attached to the delivery wire when deployed at the puncture site 100 and during transformation from the first to the second shape. The delivery wire 50 is withdrawn, thus arranging the attachment unit 40 in the puncture opening and centering the device longitudinally in relation to the opening. This is illustrated in FIG. 8B, where the strips 31 are shown in full overlap and the guide wire detached from the aggregate 10.

When the coiled tubular member has section that are not covered by overlapping strips 31 at its en section or end sections, this provides an enhanced anchoring of the aggregate in the tissue wall 200 of the body lumen as the support member may at least partly migrate into the tissue wall.

Figure 7I:
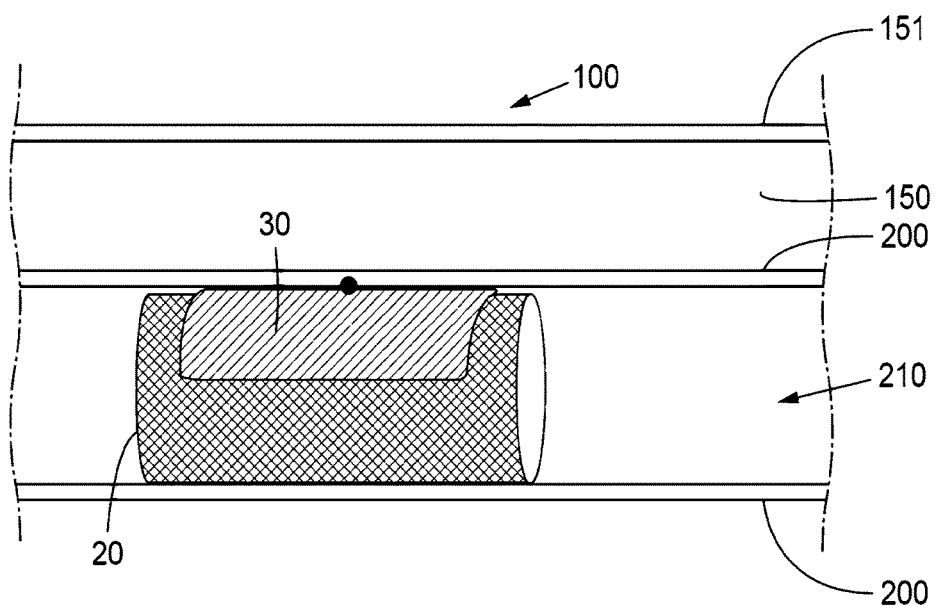
Figure 7J:
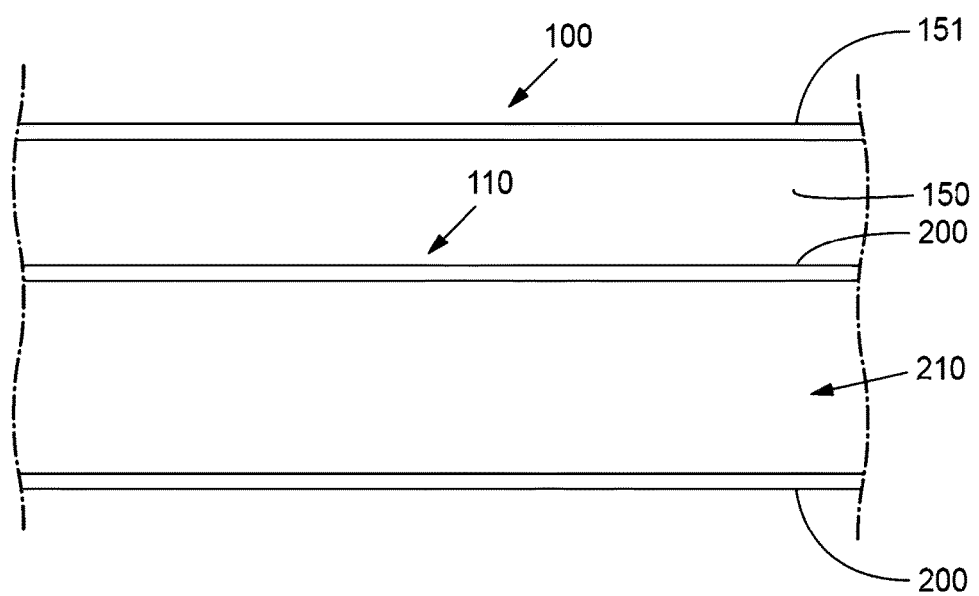
Figure 8C:
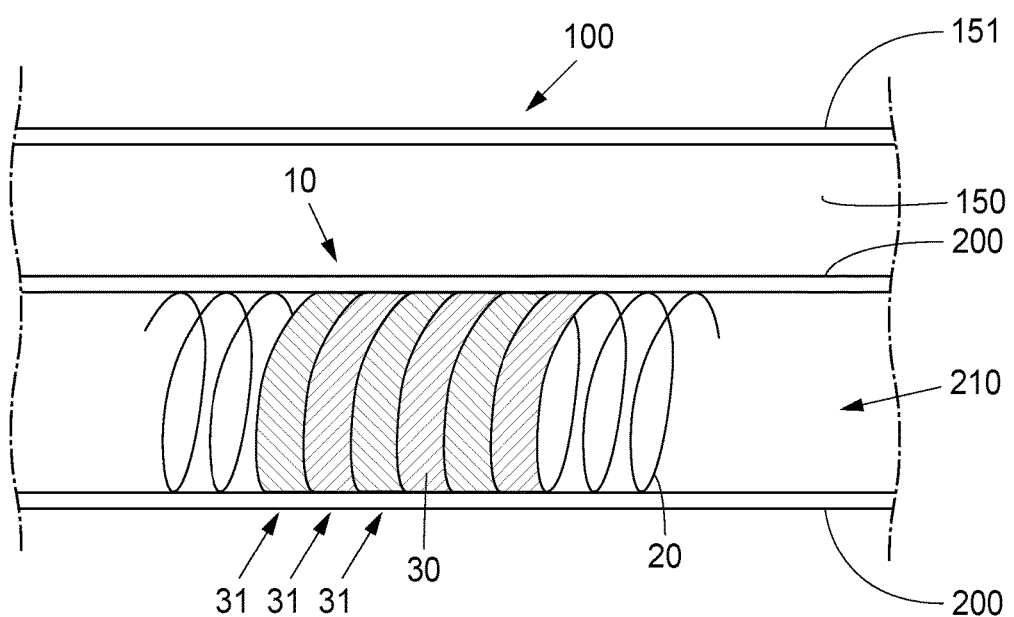
Figure 8D:
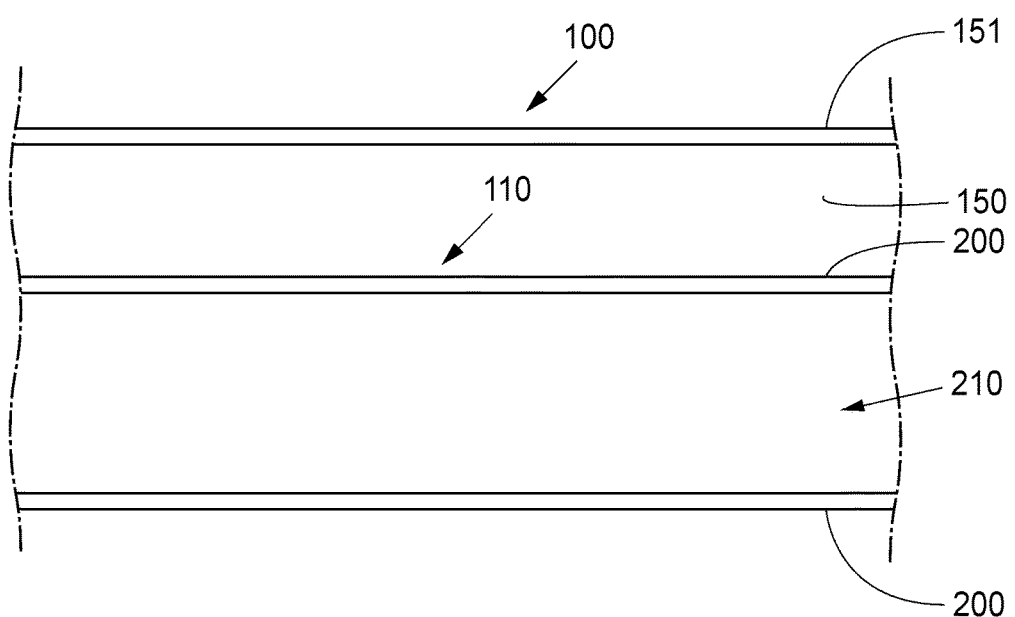

In FIGS. 8C and 8D, like in FIGS. 7I and 7J, the puncture site is shown healed and the device resorbed, respectively.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention as defined by the patent claims.

For instance the attachment unit 40 may be integrated in the patch member 30, e.g. in form of a loop, ring, etc. The attachment unit may be non-protruding. The attachment unit may be part of the delivery unit and removed therewith upon closure of the puncture.

Alternatively to the expansion of the aggregate as described above and illustrated in the Figs., the aggregate may be first drawn towards the puncture opening 110, such that the patch member 30 abuts around the opening. The expansion of the support member may then be controllably initiated. For instance the tubular expansion may be suitably triggered, e.g. by breaking connection points by a suitable external influence.

Different method steps than those described above, even merely in a different order. The different features and steps of the invention may be combined in other combinations than those described. The scope of the invention is only limited by the appended patent claims.

The invention claimed is:

1. A method for closing a puncture opening in a body lumen of a patient by use of a medical device, said method comprising:
    delivering an aggregate comprising a support structure and a substantially fluid tight patch member through the puncture opening and into the body lumen at a site of the puncture opening, wherein said substantially fluid tight patch member is sized and shaped to be positioned against an inner tissue wall of said body lumen at the site of said puncture opening and to extend over said puncture opening;
    aligning said substantially fluid tight patch member with said puncture opening by pulling on a delivery wire attached to said aggregate, said delivery wire extending from said aggregate though said puncture opening;
    at least partly initially closing said puncture opening with said substantially fluid tight patch member before said support structure changes shape from a first, delivery shape to a second, tubular shape;
    moving a circumference of said support structure towards a periphery of said substantially fluid tight patch member when changing shape from the first delivery to the second tubular shape;
    anchoring said aggregate in said body lumen by subjecting the support structure to a change in shape from said first, delivery shape to said second, tubular shape to arrange the substantially fluid tight patch member at least partly radially outside of the support structure and at least partly towards said inner tissue wall of the body lumen at the site of the puncture opening and thereby closing the puncture opening from inside the body lumen;
    wherein the periphery of the substantially fluid tight patch member is free from attachment to the support structure; and
    wherein said second, tubular shape has a larger cross sectional dimension than the first, delivery shape.

2. The method of claim 1, wherein:
    the substantially fluid tight patch member is arranged on an outside of the support structure and is attached to the support structure at an intermediate portion between ends thereof and a distal end of said delivery wire is radially and releasably attached to the aggregate and
    the method further comprises detaching the delivery wire from the aggregate after delivering the aggregate into the body lumen.

3. The method of claim 2, and further comprising detaching the delivery wire from the aggregate when said support structure is in said second, tubular shape.

4. The method of claim 3, wherein detaching the delivery wire comprises unscrewing said delivery wire from a threaded attachment on said aggregate.

5. The method of claim 1, wherein said second, tubular shape has a diameter that is larger than a diameter of said body lumen at said puncture site, and said anchoring of the aggregate results with said substantially fluid tight patch member being arranged radially outside the support structure extending over the puncture opening.

6. The method of claim 1, wherein the delivery wire is releasably attached to said aggregate.

7. The method of claim 1, and further comprising extending the substantially fluid tight patch member partly into a puncture channel at said puncture opening.

8. The method of claim 1, wherein the change in shape of the support structure comprises self expanding the support structure in the body lumen and the support structure is made of a self expanding material.

9. The method of claim 1, wherein said support structure is made of a shape memory material, said first delivery shape is an elongate shape, and said second, tubular shape is a helically coiled shape.

10. The method of claim 1, and further comprising controlling, activating, and/or de-activating said subjecting the support structure to a change in shape.

11. The method of claim 10, wherein said controlling, activating, or deactivating said change of shape is accomplished by means of a connection element forming a connection to the support structure between a first and second part of said support structure and said method further comprises breaking said connection.

12. The method of claim 1, wherein a physiological pressure of a body fluid in said body lumen on the substantially fluid tight patch member holds said substantially fluid tight patch member against a wall of said body lumen.

13. The method of claim 1, wherein said aligning comprises arranging the aggregate such that said support structure is arranged symmetrically in said body lumen in relation to said puncture opening site.

14. The method of claim 1, wherein said delivering comprises introducing the aggregate into the body lumen through an introducer sheath at said puncture opening site and said method further comprises removing said introducer from the puncture opening site upon deployment of said aggregate.

15. The method of claim 1, and further comprising delivering a pharmaceutical agent to the puncture opening site by way of the aggregate comprising the pharmaceutical agent.

16. The method of claim 1, wherein the aggregate comprises a pharmaceutical agent adapted to prohibit a thickening of a wall of the body lumen and the method further comprises prohibiting the thickening of the wall of said body lumen by the elution of the pharmaceutical agent from the aggregate.

17. The method of claim 1, wherein the aggregate comprises one or more pharmaceutical agents selected from an endothelial growth promoting agent, a fibrosis promoting agent, a scar reducing agent, an anti-pathogenic agent, and anti-infectious agent, an anticoagulant, and an anti-thrombotic agent and wherein the method further comprises one or more of:
promoting endothelial cell growth over the aggregate;
promoting fibrosis at the puncture opening;
preventing or reducing scar tissue at said puncture opening site;
preventing or reducing infection;
preventing coagulation of a body fluid in the body lumen; and
preventing thrombosis in the body lumen.

18. The method of claim 1, and further comprising re-enforcing a wall and supporting a patency of the body lumen at the puncture opening site.

19. The method of claim 18, further comprising re-puncturing the body lumen at the puncture site.

20. The method of claim 1, wherein the body lumen is a lumen in: an arterial blood vessel, a peripheral blood vessel, an arteria subclavia, an arteria axillaris, a region near a clavicle, an aorta, an ascendant aorta, a descendent aorta, a branch of an aorta, a component of a urinary tract, a component of a gastrointestinal tract, a bile duct, a liver, a kidney, a lymphatic system, or a central nervous system.

21. The method of claim 1, and further comprising sealing said puncture opening by said substantially fluid tight patch member by drawing said delivery wire in a direction out of said puncture opening and tightening said substantially fluid tight patch member over said puncture opening before said support structure changes shape from the first, delivery shape to the second, tubular shape.

22. A method for closing a puncture opening in a body lumen of a patient by use of a medical device, said method comprising:
advancing a catheter through an opening of a body lumen;
releasing an aggregate from said catheter and into said body lumen; said aggregate comprising a support structure and a patch being substantially fluid tight and extending less than a circumference of said support structure; said patch being attached to said support structure near a central portion of said patch such that a periphery of said patch is free from attachment to said support structure;
withdrawing a delivery wire so as to draw an attachment point between said aggregate and said delivery wire to said opening of said body lumen;
aligning said patch across said opening of said body lumen; and,
changing a shape of said support structure from a compressed first delivery shape to a tubular, radially expanded, second delivery shape; said second delivery shape anchoring said aggregate in said lumen of said body.

* * * * *